United States Patent [19]

Nakagawa et al.

[11] Patent Number: 4,978,430

[45] Date of Patent: Dec. 18, 1990

[54] METHOD FOR DEHYDRATION AND CONCENTRATION OF AQUEOUS SOLUTION CONTAINING ORGANIC COMPOUND

[75] Inventors: Kanji Nakagawa; Yoshio Asakura; Shigeru Yamamoto; Kohei Ninomiya; Masayuki Kinouchi, all of Ichihara, Japan

[73] Assignee: UBE Industries, Ltd., Ube, Japan

[21] Appl. No.: 384,878

[22] Filed: Jul. 24, 1989

Related U.S. Application Data

[63] Continuation of Ser. No. 7,128,818, Dec. 1, 1987, abandoned.

[30] Foreign Application Priority Data

| Dec. 6, 1986 | [JP] | Japan | 61-290832 |
| Jan. 12, 1987 | [JP] | Japan | 62-4730 |
| Mar. 6, 1987 | [JP] | Japan | 62-51469 |
| Sep. 11, 1987 | [JP] | Japan | 62-228193 |

[51] Int. Cl.$^5$ .......................... B01D 3/00; B01D 13/00
[52] U.S. Cl. .............................. 203/014.000; 564/437; 564/497; 568/410; 568/411; 568/810; 568/835; 568/868; 568/916; 203/15; 203/16; 203/17; 203/18; 203/19; 203/39; 203/DIG. 13; 203/91; 159/DIG. 27; 210/500.23; 210/500.39; 210/640; 549/377; 549/429; 560/248; 562/606; 562/608; 562/609
[58] Field of Search ................... 203/19, 18, DIG. 13, 203/99, 89, DIG. 16, 39, 14–17, 91; 159/DIG. 27, DIG. 28; 210/640, 500.39, 500.23; 564/437, 497; 568/916, 410, 411, 872, 868, 810, 835; 549/377, 429; 562/606, 608, 609; 560/248

[56] References Cited

U.S. PATENT DOCUMENTS

| 2,386,826 | 10/1945 | Wallach et al. | 210/640 |
| 2,583,601 | 1/1952 | Schwertz | 159/DIG. 27 |
| 3,035,060 | 5/1962 | Binning et al. | 210/640 |
| 3,043,891 | 7/1962 | Stuckey | 210/640 |
| 3,303,105 | 2/1967 | Konikoff et al. | 210/640 |
| 3,455,792 | 7/1969 | Ohta | 202/200 |
| 4,067,805 | 1/1978 | Chiang et al. | 210/640 |
| 4,405,409 | 9/1983 | Tusel et al. | 203/19 |
| 4,440,643 | 4/1984 | Makino et al. | 210/500.39 |
| 4,474,858 | 10/1984 | Makino et al. | 210/500.39 |
| 4,523,041 | 7/1985 | Shuey et al. | 210/500.39 |
| 4,620,900 | 11/1986 | Kimura et al. | 159/DIG. 27 |
| 4,717,394 | 1/1988 | Hayes | 210/500.39 |

FOREIGN PATENT DOCUMENTS

| 58-21629 | 2/1983 | Japan | 568/916 |
| 58-92420 | 6/1983 | Japan | 210/500.39 |
| 60-28803 | 2/1985 | Japan | 210/500.39 |
| 60-202705 | 10/1985 | Japan | 203/39 |
| 63-258602 | 10/1988 | Japan | 203/39 |
| 1564870 | 7/1977 | U.S.S.R. | 203/19 |

*Primary Examiner*—Wilbur Bascomb
*Attorney, Agent, or Firm*—Frishauf, Holtz, Goodman & Woodward

[57] ABSTRACT

An improved method for dehydration and concentration of an aqueous solution containing an organic compound is disclosed. The solution is evaporated to produce a gaseous mixture comprising an organic compound vapor and a water vapor. The water vapor is selectively removed from the gaseous mixture by permeation through an aromatic polyimide gas separation membrane while the gaseous mixture being kept in contact with a surface on one side of the gas separation membrane at a temperature of 70° C. or higher to obtain a gaseous mixture comprising the organic compound vapor and a reduced amount of a water vapor.

16 Claims, 2 Drawing Sheets

METHOD FOR DEHYDRATION AND CONCENTRATION OF AQUEOUS SOLUTION CONTAINING ORGANIC COMPOUND

This application is a continuation of application Ser. No. 07/128,818 filed Dec. 4, 1987 now abandoned.

BACKGROUND OF THE INVENTION

1. Field of the Invention

This invention relates to a method for dehydration and concentration of an aqueous solution containing an organic compound by vapor phase separation.

2. Description of Prior Art

A distillation method is generally employed as a method to dehydrate an aqueous solution containing an organic compound. For dehydrating an azeotropic mixture or a mixture of water and an organic compound having a boiling point similar to water which is hardly separated in a general distillation method, an azeotropic distillation method or an extractive distillation method is used.

For example, an ethanol-containing product produced from a biomass is processed in the following manner. The ethanol content in the product produced from a biomass is not more than 10 weight %, and hence ethanol is first concentrated to give an azeotropic composition of 95.6 weight % in a first distillation column by distillation. Subsequently, an entrainer such as benzene which produces in combination with water an azeotropic composition having a boiling point lower than ethanol is added to the concentrated product. A pure ethanol is then prepared by subjecting the resulting mixture by azeotropic distillation in a second distillation column to remove the azeotropic composition. In this process, the azeotropic distillation in the second distillation column requires a large energy to remove a slight amount of water.

As an improved method for dehydration of an organic solvent using less energy, a pervaporation method has been proposed. In this method, water vapor is selectively permeated employing a gas separation membrane by supplying an organic solution to one side of the gas separation membrane, while reducing pressure or supplying a carrier gas on another side of the membrane. However, the pervaporation method has problems in lowering of selective permeability and duration in the course of use for a long period of time, because the gas separation membrane is kept in direct contact with the organic solution and the membrane is apt to swell.

Further, a vapor-phase dehydration method has been proposed. This method employs a gas separation membrane to permeate a water vapor selectively by supplying a gaseous mixture comprising an organic compound vapor and a water vapor (which is produced by evaporation of an aqueuous solution containing an organic compound) on one side of the gas separation membrane, while keeping another side under reduced pressure or causing an inert gase as a carrier gas flowing on the surface of the membrane on another side. A method which employs a ceramic porous hollow fiber membrane is described in "Membrane" 10(5), 297 (1985, written in Japanese). The method which employs a gas permeation membrane of polyamide, cellulose or cellulose acetate is described in Japanese Patent Provisional Publication No. 60(1985)-99314.

In the method employing a ceramic porous hollow fiber membrane, the hollow fiber membrane does not swell, because the membrane is an inorganic material. However, it is disadvantageous that the ceramic porous hollow fiber is fragile to be broken easily. Further, it is difficult to form a fine hollow fiber membrane from an inorganic material. If the inorganic membrane in the form of a thick hollow fiber membrane is charged for manufacture of a module, the resulting effective membrane area capable of serving as permeation area is small and hence the membrane of an inorganic material has a problem in practical use.

Japanese Patent Provisional Publication No. 60(1985)-99314 describes a method employing a gas permeation membrane of an organic polymer of polyamide, cellulose or cellulose acetate. To dehydrate a gaseous mixture comprising an organic compound vapor and a water vapor, it is generally necessary to perform dehydration at a temperature higher than the boiling point of the organic compound-containing solution. Therefore, the gas separation membrane requires high thermal resistance and high organic solvent resistance (i.e., resistance to an organic solvent). However, the organic polymer membrane such as polyamide, cellulose or cellulose acetate, etc. is insufficient in thermal resistance and organic solvent resistance, and especially has a problem of stability of selective permeability in a long term operation. Further, the organic polymer membrane is insufficient in a permeation rate of a water vapor and selective permeability of a water vapor against a gas of an organic compound.

SUMMARY OF THE INVENTION

An object of the present invention is to provide an improved method for dehydration and concentration of an aqueous solution containing organic compound, wherein the organic compound is evaporated to produce a gaseous mixture comprising an organic compound vapor and a water vapor, and the water vapor is removed from the gaseous mixture by selective permeation using a gas separation membrane to obtain a gaseous mixture containing an organic compound vapor and a reduced amount of a water vapor.

There is provided by the present invention a method for dehydration and concentration of an aqueous solution containing an organic compound, wherein the aqueous solution is evaporated to produce a gaseous mixture comprising an organic compound vapor and a water vapor, and the water vapor is selectively removed from the gaseous mixture by permeation through an aromatic polyimide gas separation membrane while the gaseous mixture being kept in contact with a surface on one side of the gas separation membrane at a temperature of 70° C. or higher to obtain a gaseous mixture comprising the organic compound vapor and a reduced amount of a water vapor.

There is also provided by the invention a method for dehydration and concentration of an aqueous solution containing an organic compound, which comprises the steps of:

evaporating the aqueous solution in an evaporation vessel to produce a gaseous mixture comprising an organic compound vapor and a water vapor;

selectively permeating the water vapor by bringing the gaseous mixture into contact with a surface on one side of an aromatic polyimide gas separation membrane at a temperature of not lower than 70° C. and reducing pressure on another side of the gas separation membrane to obtain a gaseous mixture comprising the organic compound vapor and a reduced amount of a water vapor;

condensing the gaseous mixture which has been selectively permeated through the gas separation film; and returning back the condensed mixture to the evaporation vessel.

There is further provided by the invention a method for removal of water from a reaction mixture comprising a reactant, a reaction product and water, said water having been produced by a chemical reaction, which comprises the steps of:

evaporating a portion of the reaction mixture to produce a gaseous mixture containing a water vapor;

removing the water vapor by bringing the gaseous mixture into contact with a surface on one side of an aromatic polyimide gas separation membrane to selectively permeate the water vapor through the separation membrane into another side so that a gaseous mixture containing a reduced amount of a water vapor is obtained; and returning back the gaseous mixture containing a reduced amount of a water vapor to the reaction mixture.

DETAILED DESCRIPTION OF THE INVENTION

Figure 1:
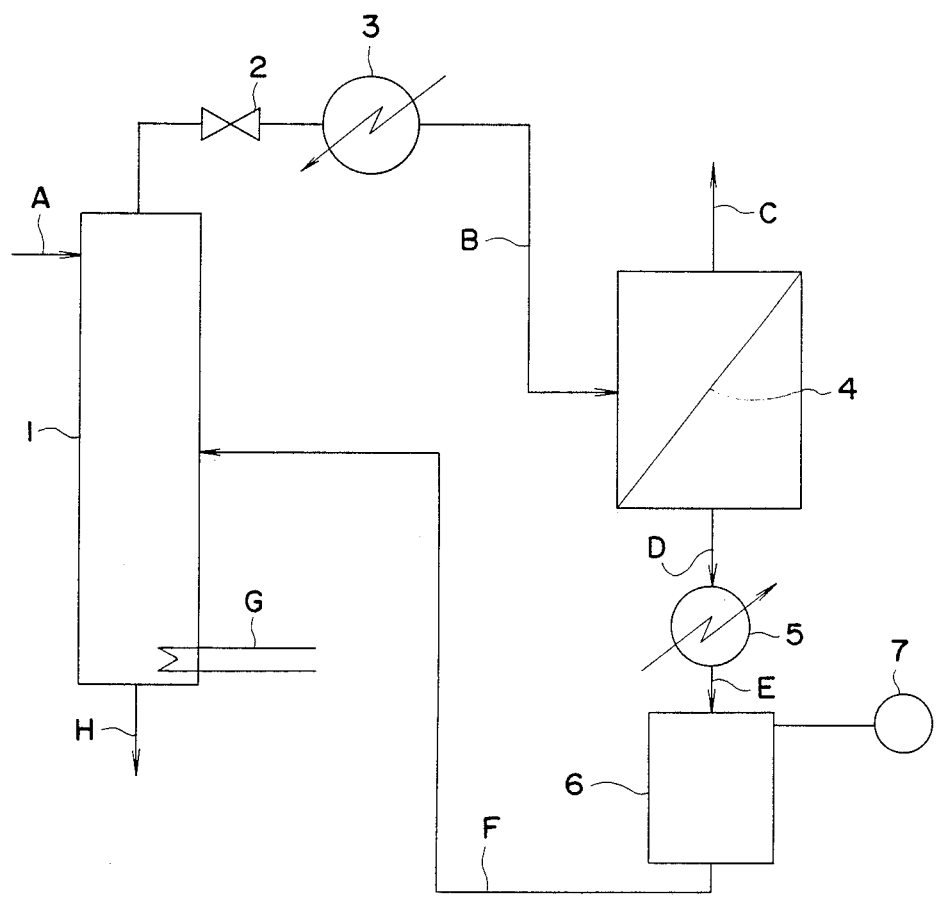
FIG. 1 is a flow sheet showing a favorable embodiment of a method for dehydration and concentration of an organic compound-containing solution according to the present invention.

The organic compound to which is applicable the present invention has a boiling point of not higher than 200° C., preferably not higher than 150° C. The organic compound preferably is in the form of a liquid at an ambient temperature, i.e., 25° C. Examples of the organic compounds include aliphatic alcohols such as methanol, ethanol, n-propanol, isopropanol, n-butanol, sec-butanol, tert-butanol and ethylene glycol; alicyclic alcohols such as cyclohexanol; aromatic alcohols such as benzyl alcohol; organic carboxylic acids such as formic acid, acetic acid, propionic acid and butyric acid; esters such as butyl acetate and ethyl acetate; ketones such as acetone and methyl ethyl ketone; cyclic ethers such as tetrahydrofuran and dioxane; and organic amines such as dibutyl amine and aniline.

The present invention is utilized for dehydration of an aqueous solution containing an alcohol optionally selected from the above organic compounds. More particularly, the invention is especially favorably utilized for dehydration of a solution containing ethanol or isopropanol.

There is no specific limitation with respect to the content of the organic compound in the aqueous solution, but the content preferably is not less than 50 weight %, and more preferably not less than 90 weight %.

This invention is characterized in that an aromatic polyimide gas separation membrane is employed as a gas separation membrane in the method for separation of an organic compound vapor from a water vapor.

In the known pervaporation process, a temperature on a primary side (gas supplying side) is necessary to be not higher than a boiling point of an organic compound to be supplied so that the organic compound-containing solution is brought into contact with a gas separation membrane in a liquid state. In the present invention, a temperature on the primary side is not less than a boiling point of the organic compound, generally is not less than 70° C., because the organic compound-containing solution is supplied to the gas separation membrane after evaporation. When the gaseous mixture comprising the organic compound vapor and the water vapor is compressed to raise its temperature in order to enlarge the difference of partial pressure of the water vapor between on the primary side and on another side of the gas separation membrane, the permeation operation is performed at a higher temperature.

In the present invention, the water vapor is selectively permeated through the gas separation membrane by keeping the atmosphere on a secondary side of the separation membrane (another side, i.e., a side from which the water-rich gas is recovered) under reduced pressure to generate enlarged difference of the partial pressure of the water vapor between both sides of the gas separation membrane. Therefore, the water vapor is selectively removed from the gaseous mixture which is supplied to the membrane on the primary side. If the pressure on the secondary side is more reduced, the permeation rate increases. It is preferred to keep the pressure on the secondary side at such a degree that a gaseous mixture recovered on the secondary side does not condense. In order to generate the necessary reduced pressure, the pressure on the secondary side of the membrane is generally kept at not higher than 200 mmHg, and more preferably not higher than 100 mmHg.

Instead of keeping the secondary side under reduced pressure, a dry inert gas (i.e., carrier gas) can be caused to flow on the surface of the secondary side of the membrane for permeating the water vapor selectively.

An aromatic polyimide gas separation membrane is known as a gas separation membrane which is improved in thermal resistance and organic solvent resistance. The aromatic polyimide membrane is heretofore employed for separation of carbon dioxide, hydrogen and carbon monoxide from a gaseous mixture, as well as for separation of water vapor from the gaseous mixture comprising gaseous methane and water vapor. However, it has not been known that the aromatic polyimide gas separation membrane can be used for separation of water vapor from a gaseous mixture comprising an organic compound existing in the form of a liquid at an ambient temperature (approx. 25° C.) and water vapor.

The aromatic polyimide gas separation membrane used in the present invention enables to manufacture a small-sized gas separation apparatus, because the aromatic polyimide gas separation membrane shows a high permeation rate of water vapor and improved selective permeability for water vapor. The aromatic polyimide gas separation membrane can be advantageously employed when it is heated higher than the boiling point of the organic compound or when a gaseous mixture comprising an organic compound vapor and a water vapor is heated by compression to enlarge the difference of partial pressure of the water vapor on both sides of the gas permeation membrane, because the aromatic polyimide membrane shows high thermal resistance as well as high organic solvent resistance. Further, the aromatic polyimide can be continuously used for a long period of time without lowering of the selective permeability at a high temperature.

The aromatic polyimide gas separation membrane shows a high permeation rate for water vapor and high selective permeability for water vapor to other organic compound vapors. The permeation rate of water vapor (P'[$H_2O$]) preferably is as high as possible to efficiently dehydrate the organic compound-containing aqueous solution continuously. When the separation is performed, the permeation rate of water vapor is preferably not lower than $0.5 \times 10^{-3}$ cm$^3$/cm$^2$·sec·cmHg. A permeation rate of lower than the above value is not preferred to obtain an organic compound vapor because the dehydration requires a long period of time, which apparently is very disadvantageous for industrial use. To increase the efficiency of the dehydration, the ratio of permeation rate of the water vapor to permeation rate of an organic compound vapor is preferably as large as possible. When the separation procedure is performed, a ratio of water vapor permeation rate (P'[$H_2O$]) to ethanol permeation rate (P'[$C_2H_5OH$]) at 100° C. (selective permeability: P'[$H_2O$]/P'[$C_2H_5OH$]) is preferably not less than 20. When the ratio is lower than this value, loss of the organic compound vapor by peameation is very large. This means that the commercial value of the present invention is lowered from a view point of industrial use.

The thickness of the aromatic polyimide gas separation membrane is preferably from 10 μm to 200 μm. The aromatic polyimide gas separation membrane is preferably used in a form of a module which is formed by binding hollow fibers having a larger effective membrane area. A spiral membrane and a plain membrane can also be used.

The hollow fiber employable as a gas separation membrane generally has an outer diameter of 50 to 2,000 μm, and preferably 200 to 1,000 μm. If the outer diameter of the hollow fiber is too small, pressure drop becomes too large. If the outer diameter is too large, the effective membrane area becomes too small. The hollow fiber preferably has a ratio of its thickness of membrane to its outer diameter in the range of 0.1 to 0.3. The thickness of membrane is defined by the following equation:

$$\text{thickness} = \frac{\text{(outer diameter)} - \text{(inner diameter)}}{2}$$

If the thickness of the wall of the hollow fiber is too thin, pressure resistance thereof is insufficient. If the thickness of the hollow fiber is too thick, the selective permeability for water vapor is insufficient.

The aromatic polyimide gas separation membrane is a gas separation membrane having an asymmetrical structure (a membrane comprising a homogeneous layer and a porous layer which is combined to give an integrated structure) which is prepared by a wet process using a solidifying solution, for instance, using a solution containing an aromatic polyamic acid (or aromatic polyimide) obtained by polymerizing an acid component such as an aromatic tetracarboxylic acid or an aromatic tetracarboxylic dianhydride and an aromatic diamine component. Alternatively, the aromatic polyimide gas separation membrane may be a composite separation membrane which is prepared by forming the thin aromatic polyimide homogeneous layer on a surface of a porous membrane of an appropriate material using a solution containing an aromatic polyimide, said gas separation membrane having a sufficient function for water vapor separation.

An aromatic tetracarboxylic (acid) skeleton of the aromatic polyimide can be derived from 3,3', 4,4'-benzophenonetetracarboxylic acid, 2,3,3',4'-benzophenonetetracarboxylic acid, pyromellitic acid, 3,3',4,4'-biphenyltetracarboxylic acid and 2,3,3',4'-biphenyltetracarboxylic acid, or dianhydrides, esters or salts of these aromatic tetracarboxylic acids.

Particularly preferred is an aromatic polyimide gas separation membrane having a main acid skeleton derived from a biphenyltetracarboxylic dianhydride such as 3,3',4,4'-biphenyltetracarboxylic dianhydride or 2,3,3'4'-biphenyltetracarboxylic dianhydride.

An aromatic diamine skeleton of the aromatic polyimide can be derived from p-phenylenediamine, m-phenylenediamine, 2,4-diaminotoluene, 3,5-diaminobenzoic acid, 3,4'-diaminodiphenyl ether, 4,4'-diamino diphenyl ether, 4,4'-diaminodiphenyl methane, o-tolidine, 1,4-bis(4-aminophenoxy)benzene, 1,3-bis(4-aminophenoxy)benzene, o-tolidinesulfone, bis(aminophenoxyphenyl)methane or bis(aminophenoxyphenyl)sulfone.

Particularly, it is preferred that at least one diamine selected from the group consisting of 3,4'-diaminodiphenyl ether, 4,4'-diaminodiphenyl ether and diaminodiphenylmethane is employed as the aromatic diamine skeleton, because each of the permeation rate of the water vapor (P'[$H_2O$]) and the selective peameability for water vapor to ethanol (P'[$H_2O$[/P'[$C_2H_5OH$]) is respectively improved, and the thermal resistance increases.

These favorable characteristics are remarkable when 3,4'-diaminodiphenyl ether or 4,4'-diaminodiphenyl ether is used singly or in combination with 4,4'-diaminodiphenylmethane. Where the diamino diphenyl ether is used in combination, the amount of 3,4'-diaminodiphenyl ether and/or 4,4'-diaminodiphenyl ether is preferably not less than 30 mol. % as a whole, and more preferably not less than 50 mol. %.

The aromatic polyimide gas separation membrane of the invention can be prepared by the following method. The aromatic diamine component comprising the above-mentioned aromatic diamine (one or more other aromatic diamines can be included) and the above-mentioned biphenyltetracarboxylic acid component in an equimolar ratio are polymerized in one step at a temperature of 140° C. or higher in an organic solvent of a phenol group to produce directly an aromatic polyimide. The aromatic polyimide solution (concentration: approx. 3 to 30 weight %) is used as a dope (i.e., coating solution), and the solution is coated or spread on a substrate having a temperature of 30° to 150° C. to give a dope solution layer for producing a plain membrane or extruded to form a dope solution to give a hollow fiber membrane. The solution layer is immersed into a solidifying medium to form a solidified membrane. The solvent and the solidifying medium are washed off from the solidified membrane, and the solidified membrane is heated to obtain an aromatic polyimide membrane of an asymmetrical gas separation membrane type.

Some embodiments of the method for dehydration and concentration of an organic compound-containing solution of the present invention are described below with reference to the attached flow sheet given in FIG. 1.

First, the organic compound-containing solution is evaporated using an evaporation vessel to produce a gaseous mixture comprising an organic compound vapor and a water vapor.

In more detail, the organic compound-containing aqueous solution is supplied to the top of the evaporation vessel 1 through a supplying pipe A. The solution is evaporated by the use of a heat source such as a steam which is supplied to the bottom of the evaporation vessel 1 through a heat source introducing pipe G to produce a gaseous mixture comprising an organic compound vapor and a water vapor. If the concentration of the organic compound in the supplied organic compound-containing solution is lower than the concentration of the azeotropic point, the organic compound-containing solution is concentrated. Generally, an aqueous solution containing an organic compound having a boiling point of not higher than 100° C. is favorably treated by the method of the invention, because the organic compound is concentrated in a distillate when the solution is evaporated in the evaporation vessel.

The gaseous mixture is then separated to give a gas containing the organic compound at a high concentration and a gas containing an increased amount of water vapor in the following manner, after adjusting a pressure and a temperature in the system.

The pressure and temperature of the gaseous mixture can be changed by controlling the heat source supplied to the bottom of the evaporation vessel 1 and an adjusting valve 2. The gaseous mixture is heated using a heater 3 to raise its temperature, and then the pressure and the temperature of the gaseous mixture supplied to one surface of the gas separation membrane 4 are raised to levels at which the gaseous mixture is not condensed. Therefore, the permeation amount of the vapor per the area of the gas separation membrane 4 and the concentration degree of the organic compound by the gas separation operation can be increased. From the above point of view, the pressure of the gaseous mixture preferably ranges from 760 mmHg to 5,000 mmHg, and the temperature preferably ranges from 70° C. to 150° C.

In the conventional pervaporation method, the organic compound-containing solution is supplied to the separation membrane in a liquid state, the permeation amount can not be increased by raising its temperature and/or by applying pressure to the membrane. In the invention, the premeation amount of the water vapor can be increased by operating the gas separation procedure at an elevated temperature and an elevated pressure.

In the conventional pervaporation method, it is necessary that the temperature of the primary side of the gas separation membrane is not higher than the boiling point in order to bring the organic compound-containing solution into contact with the gas separation membrane in a liquid state. According to the present invention, the temperature on the primary side of the gas separation membrane is adjusted to a temperature not lower than the boiling point of the organic compound or its solution, usually not lower than 70° C. in order to supply the organic compound-containing aqeous solution to the gas separation membrane in a gas state. When a gaseous mixture comprising an organic compound vapor and a water vapor is pressed in order to enlarge difference of the partial pressure of the water vapor on both sides of the gas separation membrane, the procedure proceeds at an elevated temperature.

The gaseous mixture of which pressure and the temperature as above is controlled is then supplied to the primary side of the gas separation membrane 4 through a gaseous mixture supplying pipe B.

When the gaseous mixture is supplied to the primary side, the difference of the partial pressure of water vapor can be enlarged by keeping the secondary side of the gas separation membrane under reduced pressure. In the case that the pressure on the secondary side of the gas separation membrane 4 is reduced, the permeation amount of the water vapor increases. The pressure on the secondary side can be reduced to a level of not condensing the gaseous mixture recovered after the permeation through the gas separation membrane. The pressure on the secondary side of the gas separation membrane 4 generally is not higher than 200 mmHg, and more preferably not higher than 100 mmHg.

The secondary side of the gas separation membrane 4 can be kept under reduced pressure using the aforementioned condenser. In more detail, the gaseous mixture containing water vapor which has been permeated into the secondary side of gas separation membrane 4 is cooled indirectly by a cooling medium (e.g., water, freon, ammonia, etc.) using a condenser 5 so that the gaseous mixture is condensed. If a vacuum pump 7 is once operated to reduce the pressure on the secondary side of the gas separation membrane 4, it is not necessary to operate the vacuum pump 7 continuously, because the reduced pressure is kept by continuously condensing the gaseous mixture by the condenser 5.

The gaseous mixture is supplied to the primary side of the gas separation membrane 4 while the secondary side is kept under reduced pressure to leave the gaseous mixture having the organic compound at an elevated concentrate on the primary side and to permeate a gaseous mixture containing an increased amount of water vapor into the secondary side.

The gaseous mixture containing the water vapor permeated into the secondary side of the gas separation membrane 4 is returned back to the evaporation vessel 1 according to the following manner.

The gaseous mixture containing an increased amount of water vapor is supplied to the condenser 5 through a exhaust pipe D, and then is condensed in the condenser 5 to obtain an aqueous solution containing a reduced amount of the organic compound. The aqueous solution containing a reduced amount of the organic compound is then supplied to a receiver tank 6 through a delivery pipe E, and then the condensed gaseous mixture (i.e., aqueous liquid) is returned back to the evaporation vessel 1 at its middle height portion through a returning pipe F of the receiver tank 6.

The aqueous solution containing a reduced amount of the organic compound is rectified utilizing an ascending vapor current which is produced by a heat source such as steam supplied to the bottom of the evaporation vessel 1 through the heat source introducing pipe G, and then is recovered as the gaseous mixture comprising the organic compound vapor and the water vapor to be combined with an organic compound-containing solution freshly supplied to the top of the evaporation vessel 1 through the supplying pipe A. The water which contains almost no organic compound is discharged through an exhaust pipe H arranged at the bottom of the evaporation vessel 1.

Accordingly, the organic compound of a high purity can be recovered through a condensed organic compound recovering pipe C.

As described above, the method of the invention can be also employed for removal of water from the chemical reaction system which produces water as a reaction product (removal of the produced water). The method for removal of the produced water is favorably applicable to the equilibrium reaction system such as reactions for the production of an ester from an alcohol and a carboxylic acid, the production of an acetal from an alcohol and an aldehyde, the production of an oxime from an aminoalcohol and a carboxylic acid and the production of an alcoholate from an alcohol and an alkali.

An embodiment of the method for removal of the produced water is described below with reference to the attached flow sheet given in FIG. 2.

First, a portion of a liquid mixture comprising a starting material, a reaction product and water produced by the reaction is evaporated to produce a gaseous mixture containing the water vapor in the following manner.

The starting material is introduced into a reaction tank 11 through a starting material introducing pipe A, and then the starting material is reacted in the reaction tank 11 to obtain a liquid mixture comprising the starting material and the reaction product while the reaction tank 11 is heated by a heat source such as steam through a heat source supplying pipe 19. The liquid mixture is heated indirectly, and a portion of the liquid mixture is evaporated, and then a gaseous mixture containing a water vapor can be obtained.

The gaseous mixture containing a water vapor is supplied through a delivery pipe B, and then is heated to raise its temperature using a heater 12 to a level of not condensing the gaseous mixture. Subsequently, the water vapor in the gaseous mixture is selectively permeated through a gas separation membrane 13 by supplying the gaseous mixture on its primary side 13a while the secondary side 13b is kept under reduced pressure to obtain a gaseous mixture containing a reduced water vapor content on the primary side 13.

The gaseous mixture containing increased amount of a water vapor permeated into the secondary side 13b of the gas separation membrane 13 is transferred into a condenser 16 through a delivery pipe E, and the gaseous mixture is condensed in the condenser 16. Accordingly, the secondary side 13b of the gas separation membrane 13 can be kept under reduced pressure. Since the secondary side 13b is kept under reduced pressure by continuously condensing the gaseous mixture containing increased amount of a water vapor in the condenser 16, it is not necessary to operate a vacuum pump 18 continuously after the vacuum pump 18 is once operated to give the reduced pressure condition. Therefore, cost for the pump operation is reduced.

The water vapor condensed in the condenser 16 is transferred as a condensate to a pressure reduction tank 17, and is supplied from the system through an exhaust pipe F. According to the above method, the water produced by the chemical reaction system is efficiently removed.

The gaseous mixture containing a reduced amount of a water vapor content obtained on the primary side 13a of the gas separation membrane 13 is transferred to a condenser 14 through a delivery line C. The gaseous mixture is condensed in the condenser 14 to obtain a liquid mixture comprising the starting material, the reaction product and water, the amount of water being reduced, and then is returned back to the reaction tank 11 through a returning pipe D.

When the pressure of the gaseous mixture supplied to the primery side 13a of the gas separation membrane 13 is increased to a level to keep the mixture from condensation, the permeation amount of water vapor increases. Therefore, if desired, the gaseous mixture is supplied under pressure to the primary side 13a of the gas separation membrane 13.

Where the pressure of the secondary side 13b is more reduced, the permeation amount of water vapor increases. The pressure is necessary to be kept at a level of keepig the permeated gaseous mixture (gaseous mixture containing an increased amount of water vapor) from condensation. The pressure in the system on the secondary side 13b of the gas separation membrane 13 is generally not higher than 200 mmHg, and preferably not higher than 100 mmHg.

In the above method, the water vapor produced by the reaction can be removed by keeping the secondary side 13b of the gas separation membrane 13 under reduced pressure when the gaseous mixture is supplied to the primary side 13a of the gas separation membrane 13. The produced water can also be removed by supplying the carrier gas to the secondary side 13b of the gas separation membrane 13, or supplying the carrier gas to the secondary side 13b of the gas separation membrane 13 while the secondary side 13b is kept under reduced pressure.

It is preferred for accomplishing the reduced pressure condition to condense the gaseous mixture containing an increased amount of a water vapor which is permeated to the secondary side 13b of the gas separation membrane 13 using condenser 16. A vacuum pump can also be used.

Figure 2:
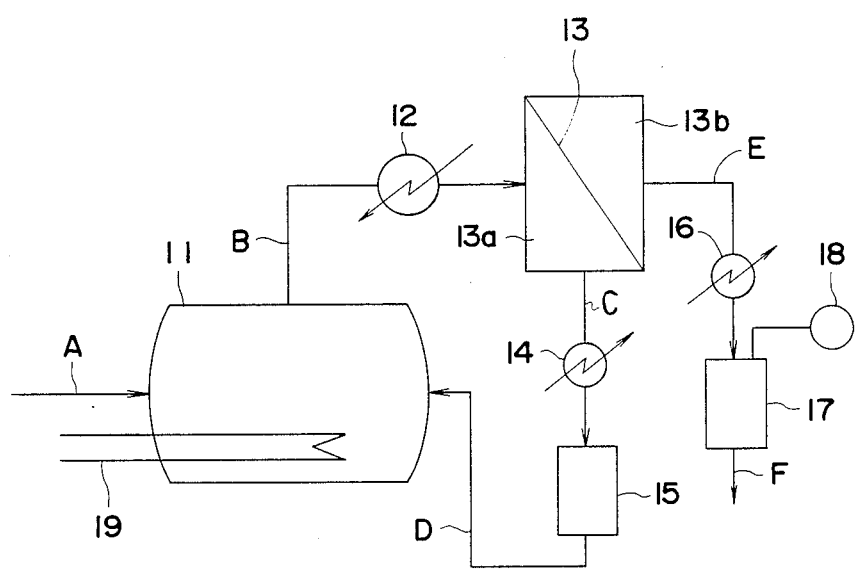
FIG. 2 is a flow sheet showing a favorable embodiment of a method for removal of water from a reaction mixture according to the invention.

In the flow sheet given in FIG. 2, when a pipe which serves for introducing the starting material continuously into the reaction tank 11 through the starting material introducing pipe A and supplys the reaction product to the reaction tank 11 is arranged, continuous removal of water can be made.

According to the method for removal of the produced water of the invention, the produced water can be easily and efficiently removed from the reaction liquid. The produced water can be removed using a less heat energy and without the use of a dehydrating agent.

The method for removal of water produced by the reaction is advantageous particularly in the following features.

(1) Since the separation procedure is performed using a gas separation membrane, handling is relatively easy, as compared with the distillation procedure.

(2) The distillation procedure is accompanied by refluxing and the refluxed mixture inherently contains a certain amount of water. Since the method of the invention removes an increased amount of the produced water, only an extremely small amount of water is returned back to the reaction mixture. Therefore, the time required for the preparation of the desired reaction product (i.e., time required to finish the reaction) can be reduced.

(3) Since the amount of heat energy consumed is reduced as compared with the distillation method, it is possible to save energy.

(4) Because the aromatic polyimide gas separation membrane is used, the thermal resistance and the organic solvent resistance is high.

(5) The method is applicable to both of batch and continuous systems.

The present invention is further described by the following examples without limiting the invention thereto.

EXAMPLE 1

A tetracarboxylic acid component consising of 100 mol. % of 3,3',4,4'-biphenyl tetracarboxylic acid dianhydride, and a diamine component consisting of 60 mol. % of 4,4'-diaminodiphenyl ether, 30 mol. % of 3,5-diaminobenzoic acid and 10 mol. % of 4,4'-diaminodiphenylmethane were polymerized to obtain an aromatic polyimide. Hollow fibers were prepared using the aromatic polyimide (outer diameter: 337 μm, inner diameter: 198 μm).

Sixteen hollow fibers were bound together and one side of the bound hollow fibers was sealed to obtain a gas separation membrane module having effective length of 5.9 cm and effective membrane area of 9.99 cm².

An aqueous solution containing 65 wt. % of ethanol was evaporated in an evaporation vessel under atmospheric pressure to obtain a gaseous mixture comprising ethanol vapor and water vapor. The gaseous mixture was introduced into the gas separation membrane module for bringing the gaseous mixture into contact with the outer surface of the hollow fiber. The temperature of the gaseous mixture was raised to 87° C., 112° C. and finally 125° C. The inside of the hollow fiber was kept under reduced pressure (4 mmHg).

By the above process, water vapor permeated into the hollow fiber was trapped by condensation in a dry ice-ethanol trap. The gaseous mixture which was not permeated into the hollow fiber was returned back to the evaporation vessel and circulated.

The ethanol concentration of the trapped condensate was analyzed by gas chromatography, and the amount of water was determined by subtracting the amount of ethanol from the whole amount of the condensate. A permeation rate of water vapor and selective permeability of water vapor to ethanol were calculated from concentration of each component, and then the gas separation efficiency was evaluated. The results are set forth in Table 1.

EXAMPLE 2

A tetracarboxylic acid component consisting of 100 mol. % of 3,3',4,4'-biphenyl tetracarboxylic acid dianhydride, and a diamine component consisting of 90 mol. % of o-tolidine sulfonic acid and 10 mol. % of 4,4'-diaminodiphenyl ether were polymerized to obtain an aromatic polyimide. Hollow fibers were then prepared using the aromatic polyimide (outer diameter: 439 μm, inner diameter: 243 μm).

Ten hollow fibers were bound together, and one side of the bound hollow fibers was sealed to obtain a gas separation membrane module having effective length of 4.7 cm and effective membrane area of 7.44 cm².

A gas separation efficiency was evaluated in the same manner as in Example 1, except that an aqueous solution containing 50 wt. % of ethanol was used in place of the aqueous solution containing 50 wt. % of ethanol, and temperatures of the gaseous mixture brought into contact with the hollow fiber were changed to 103° C., 111° C. and finally 125° C. The results are set forth in Table 1. In Table 1, a unit of "Water vapor permeation rate" is given in term of cm³/cm²·sec·cmHg. "Selective permeability" is a value of selective permeability of water vapor to ethanol and represeted by a ratio of permeation rate.

TABLE 1

|  | Temperature of gaseous mixture (°C.) | Reduced pressure (mmHg) | Water vapor permeation rate (P'[$H_2O$] × $10^{-3}$) | Selective permeability (P'[$H_2O$]/ P'[$C_2H_5OH$]) |
|---|---|---|---|---|
| Example 1 | 87 | 4 | 1.50 | 41 |
|  | 112 | 4 | 0.70 | 100 |
|  | 125 | 4 | 0.57 | 255 |
| Example 2 | 103 | 4 | 1.63 | 25 |
|  | 111 | 4 | 1.44 | 42 |
|  | 125 | 4 | 1.23 | 70 |

EXAMPLE 3

Hollow fibers having the same constitution as in Example 1 were prepared (outer diameter: 1,000 μm, inner diameter: 666 μm).

The hollow fibers were bound together and one side of the bound hollow fibers was sealed to obtain a gas separation membrane module having effective length of 150 cm and effective membrane area of 1.0 m².

An aqueous solution containing 50 wt. % of ethanol was evaporated using an evaporation vessel to obtain a gaseous mixture comprising ethanol vapor and water vapor. The gaseous mixture was heated to 100° C. and brought into contact with the outer surface of the hollow fibers at a rate of 0.36 Nm³/hour. The inside of the hollow fiber was kept under reduced pressure (20 mmHg).

By the above process, water vapor permeated into the hollow fiber was trapped by condensation in a dry ice-ethanol trap. An aqueous solution containing 11.7 wt. % of ethanol was obtained in the condensation trap at a rate of 234.7 g/h. An ethanol vapor which was concentrated up to 99.5 weight % above the concentration of the azeotropic composition was obtained on the outlet of the gaseous mixture which was not permeated into the hollow fiber at a rate of 0.089 Nm³/h.

EXAMPLE 4

100 g of an aqueous solution containing 50 wt. % of ethanol was evaporated in an evaporation vessel under atmosphere pressure to obtain a gaseous mixture comprising ethanol vapor and water vapor. The gaseous mixture was heated to 100° C. and brought into contact with the gas separation membrane module in the same manner as in Example 1. The inside of the hollow fiber was kept under reduced pressure of 4 mmHg, and the vapor permeated into the inside of the hollow fiber was trapped by condensation in a dry ice-ethanol trap. The gaseous mixture which was not permeated into the hollow fiber was returned back to the evaporation vessel and circulated.

After 36 hours, the residual solution in the evaporation vessel amounted to 67.9 g, and the ethanol concentration reached 70.5 weight %. From the permeated gaseous mixture, 30.7 g of an aqueous solution containing 3.7% of ethanol was proeuced in a condensation trap.

EXAMPLE 5

99.8 g of an aqueous solution containing 94.3 wt. % of ethanol was evaporated in an evaporation vessel under atmospheric pressure to obtain a gaseous mixture comprising ethanol vapor and water vapor. The gaseous mixture was heated to 102° C. and brought into contact with the gas separation membrane module in the same manner as in Example 1. The inside of the hollow fiber was kept under reduced pressure of 3 mmHg, and the vapor permeated into the inside of the holllow fiber was trapped in a dry ice-ethanol trap. The gaseous mixture which was not permeated into the hollow fiber was returned back to the evaporation vessel and circulated.

After 31 hours, the residual solution of ethanol in the evaporation vessel amounted to 92.4 g and the ethanol concentration reached 97.9 weight % above the concentration of the azeotropic composition. From the permeated gaseous mixture 5.3 g of an aqueous solution containing 34.2% of ethanol was produced in a condensation trap.

EXAMPLE 6

An aqueous solution containing 65 wt. % of ethanol was evaporated in evaporation vessel under atmospheric pressure to obtain a gaseous mixture comprising ethanol vapor and water vapor. The gaseous mixture was heated to 100° C. and brought into contact with the gas separation membrane module in the same manner as in Example 1. The inside of the hollow fiber was kept under reduced pressure of 4 mmHg, and the vapor permeated into the inside of the holllow fiber was trapped in a dry ice-ethanol trap. The gaseous mixture which was not permeated into the hollow fiber was returned back to the evaporation vessel and circulated.

The evaporation procedure was operated for 500 hours and change of the permeation rate of water vapor and the selective permeability of water vapor to ethanol was measured. The results are set forth in Table 2.

TABLE 2

| Operation time (hour) | Temp- erature of gas (°C.) | Pressure (mmHg) | Water vapor permeation rate ($P'[H_2O]) \times 10^{-3}$ | Selective permeability ($P'[H_2O]/ P'[C_2H_5OH]$) |
|---|---|---|---|---|
| 2.3 | 100 | 4 | 0.95 | 46 |
| 6.8 | 100 | 4 | 0.92 | 64 |
| 10.8 | 100 | 4 | 0.98 | 70 |
| 14.5 | 100 | 4 | 0.98 | 72 |
| 20.3 | 100 | 4 | 1.11 | 109 |
| 24.6 | 100 | 4 | 1.09 | 123 |
| 29.0 | 100 | 4 | 1.03 | 115 |
| 32.4 | 100 | 4 | 1.06 | 123 |
| 52.6 | 100 | 4 | 0.96 | 119 |
| 74.0 | 100 | 4 | 0.99 | 143 |
| 122.2 | 100 | 4 | 1.03 | 187 |
| 150.0 | 100 | 4 | 1.07 | 179 |
| 500.0 | 100 | 4 | 1.06 | 182 |

It is apparent from the results, the gas separation membrane of an aromatic polyimide is stably maintained for a long time.

EXAMPLE 7

Sixteen hollow fibers used in Example 1 were bound to prepare a gas separation membrane module having effective membrane area of 9.82 cm² and charged into a sealed vessel having an inlet and an outlet of a carrier gas and an inlet and an outlet of a gaseous mixture.

An aqueous solution containing 65 wt. % of ethanol was evaporated in an evaporation vessel under atmospheric pressure to obtain a gaseous mixture comprising ethanol vapor and water vapor. The gaseous mixture was heated to 90° C. and brought into contact with the outer surface of the holllow fiber by supplying the mixture to the gas separation membrane module through the gaseous mixture inlet. A carrier gas was introduced into the inside of the hollow fiber through the carrier gas inlet. The gaseous mixture of the carrier gas and permeated gaseous mixture was released through the carrier gas outlet and introduced into the dry ice-ethanol trap, and the permeated gaseous mixture was trapped by condensation. A pipe from the carrier gas outlet to the dry ice-ethanol trap was kept at 45° C. for keeping the permeated gaseous mixture from condensation therein. A gaseous mixture which was not permeated into the hollow fiber was returned back to the evaporation vessel through the gaseous mixture outlet and circulated.

The condensate was analyzed by gas chromatography, and the permeation rate of water vapor and the selective permeability of water to ethanol was calculated.

The results are set forth in Table 3.

TABLE 3

| Temperature of gaseous mixture (°C.) | Water vopor premeation rate ($P'[H_2O] \times 10^{-3}$) | Selective permeability $P'[H_2O]/ P'[C_2H_5OH]$) |
|---|---|---|
| 90 | 1.64 | 52 |

EXAMPLE 8

Aromatic polyimide hollow fibers (outer diameter: 524 μm, inner diameter: 398 μm) having the same structure in Example 1 were prepared. The gas separation performance was evaluated in the same manner as in Example 1, except that the above hollow fibers were used, an aqueous solution containing 65 wt. % of isopropanol was used in place of the aqueous solution containing 65 wt. % of ethanol and the temperature of the gaseous mixture was raised to 120° C.

The measured permeation rate of water vapor was $1.16 \times 10^{-3}$ cm³/cm²·sec.·cmHg, and the selective permeability of water to isopropanol ($P'[H_2O]/P'[i-C_3H_7OH]$) was 30,900.

EXAMPLES 9 to 14

Aromatic polyimide hollow fibers were prepared in the same manner as in Example 1, except that the aromatic polyimide obtained by polymerizing a tetracarboxylic acid component consisting of 100 mol. % of 3,3',4,4'-biphenyltetracarboxylic dianhydride and the aromatic diamine component as indicated in Table 4 was used. The gas separation performance was evaluated in the same manner as in Example 1, except that the above hollow fibers were used and the temperature of the gaseous mixture was raised to 100° C.

The results are set forth in Table 4.

Fresh hollow fibers were immersed into a boiling water heated to 150° C. for 20 hours, and each of the hollow fiber membranes before and after heating was respectively dissolved in a specific solvent. The change of logarithmic viscosity (temperature: 30° C., concentration: 0.5 g of polyimide/100 ml of solvent, solvent: o-chlorophenol/p-chlorophenol=¼, weight ratio) was measured, and then the thermal resistance of the hollow fiber was evaluated.

The results are set forth in Table 4. In Table 4, "DADE" means diaminodiphenyl ether, "DADM" means diaminodiphenylmethane and "DABA" means diaminobenzoic acid. "Rate" means water vapor permeation rate ($P'[H_2O] \times 10^{-3}$) and the value of the rate is cm³/cm²·sec·cmHg, "Permeability" means the selective permeability of water vapor to ethanol ($P'[H_2O]/P'[C_2$-

H5OH]). "Viscosity (a)" means logarithm viscosity before heating, "Viscosity (b)" means logarithm viscosity after heating, "Retention" means retention of the logarithm viscosity.

The logarithmic viscosity is represented by the following formula, and has high correlation to the molecular weight of the aromatic polyimide.

$$\text{Logarithmic viscosity} = \frac{\text{Natural logarithm (viscosity of solution/viscosity of solvent)}}{\text{Concentration of solution}}$$

Polymers having a high retention of the logarithmic viscosity after heating to the logarithmic viscosity before heating is understood to keep its molecular weight before heating. It means that the thermal resistance is high.

TABLE 4

| | 3,4'-DADE | 4,4'-DADE | 4,4'-DADM | 3,5'-DABA | Rate | Permeability | Viscosity (a) | Viscosity (b) | Retention (%) |
|---|---|---|---|---|---|---|---|---|---|
| | (molar %) | | | | | | | | |
| Ex. 9 | — | 60 | 10 | 30 | 1.47 | 22 | 1.61 | 0.73 | 45 |
| Ex. 10 | — | 100 | — | — | 0.96 | 24 | 1.74 | 1.46 | 84 |
| Ex. 11 | 100 | — | — | — | 0.91 | 1,030 | 1.52 | 1.43 | 94 |
| Ex. 12 | 60 | 40 | — | — | 1.24 | 134 | 2.09 | 1.75 | 84 |
| Ex. 13 | — | 60 | 40 | — | 0.75 | 44 | 1.73 | 1.71 | 99 |
| Ex. 14 | 60 | — | 40 | — | 1.01 | 21 | 1.90 | 1.82 | 96 |

TABLE 5

| | Temperature of gaseous mixture (°C.) | Water vapor permeation rate (P'[H$_2$O] × 10$^{-5}$) | Selective permeability (P'[H$_2$O]/P'[C$_2$H$_5$OH]) |
|---|---|---|---|
| Example 15 | 100 | 1.10 | 42 |
| | 120 | 0.85 | 140 |
| | 100 | 1.09 | 60 |
| Comparison Example 1 | 100 | 0.55 | 16 |
| | 120 | 0.37 | 19 |
| | 100 | 0.36 | 24 |

EXAMPLE 15

Hollow fibers prepared in the same manner as in Example 1 were kept in continuous contact with a heated vapor of ethanol for 1 week, and then an organic solvent resistance was evaluated. No change of appearance was observed.

The gas separation performance was evaluated in the same manner as in Example 1, except that the above hollow fibers were used, and the temperature of the gaseous mixture was raised from 100° C. to 120° C., and then lowered to 100° C. again. The results are set forth in Table 5.

The water vapor permeation rate decreases by raising the temperature of the gaseous mixture from 100° C. to 120° C., but the rate was recovered to the original rate by lowering the temperature to 100° C.

COMPARISON EXAMPLE 1

A cellulose acetate film having an acetylation degree of 39.8% and a thickness of 6 μm was immersed into ethanol at room temperature for 20 hours, and the organic solvent resistance was then evaluated. No change of appearance was observed.

The gas separation performance was evaluated in the same manner as in Example 15, except that the cellulose acetate film having effective area of 13.8 cm² was used.

The results are set forth in Table 5.

The water vapor permeation rate which decreased by raising the temperature of the gaseous mixture from 100° C. to 120° C. was not recovered even though the temperature was lowered to 100° C.

EXAMPLE 16

A dehydration procedure was performed according to the flow sheet shown in FIG. 1. In this example, the method of the invention was applied to a process comprising fermentation and purification for the preparation of ethanol with respect to the azeotropic distillation step.

An aqueous solution of ethanol having an ethanol concentration of 94 weight % was supplied to the top of the evaporation vessel 1 in an amount of 0.6 kg/h through the starting material supplying pipe A. The evaporation vessel 1 was heated by a steam at a temperature of 150° C. through the heat source introducing pipe G. A gaseous mixture comprising ethanol vapor and water vapor supplied from the evaporation vessel 1 was heated to 120° C. and pressed to 3,300 mmHg by adjusting the valve 2. The gaseous mixture comprising ethanol vapor and water vapor was further heated to 130° C. using the heater 3, and then was supplied to the primary side of the gas separation membrane 4 through the gaseous mixture supplying pipe B. An aromatic polyimide hollow fibers having an outer diameter of 500 μm and effective membrane area of 3 m² was employed as the gas separation membrane 4. Pressure of the secondary side of the gas separation membrane 4 was reduced to 100 mmHg.

The gaseous mixture having been permeated through the gas separation membrane 4 had an ethanol concentration of 49 weight %. This mixture was supplied into the condenser 5 at a rate of 1.3 kg/h through the exhaust pipe D. The gaseous mixture was cooled indirectly to condense in the condenser 5, and then was returned back to the evaporation vessel 1 through the receiver tank 6 and the returning pipe F. The pressure on the secondary side was reduced by initially operating the vacuum pump 7, but the pressure on the secondary side of the gas separation membrane 4 was kept at 100 mmHg without continuing the operation of the vacuum pump.

An aqueous solution containing 200 ppm of ethanol was supplied at a rate of 1.6 kg/h through the exhaust pipe H arranged at the bottom of the evaporation vessel 1. A gas which was not permeated the gas separation membrane 4 was recovered through the recovery pipe C to give a condensed ethanol which concentration reached to 99.5 weight % at a rate of 10 kg/h.

EXAMPLE 17

An aqueous solution having ethanol concentration of 50 weight % was condensed to a concentration of 94 weight % by an operation performed according to the flow sheet of in FIG. 1.

An aqueous solution of ethanol having an ethanol concentration of 50 weight % was supplied to the top of the evaporation vessel 1 at a rate of 18.8 kg/h through the starting material supplying pipe A. A temperature of the gaseous mixture comprising ethanol vapor and water vapor supplied from the evaporation vessel 1 was 120° C., a pressure was 2,700 mmHg, and the ethanol concentration was 77 weight %. The gaseous mixture comprising ethanol vapor and water vapor was heated to 130° C. using the heater 3, and then was supplied to the primary side of the gas separation membrane 4 through the gaseous mixture supplying pipe B. The same gas separation membrane as in Example 16 was used, except that the effective membrane area was 2 m². The pressure on the secondary side of the gas separation membrane 4 was reduced to 100 mmHg.

The gaseous mixture having permeated the gas separation membrane 4 having an ethanol concentration of 8 weight % was supplied to the condenser 5 at a rate of 2.5 kg/h through the exhaust pipe D. The gaseous mixture was cooled indirectly to condense in the condenser 5, and then was returned back to the evaporation vessel 1 through the receiver tank 6 and the returning pipe F. An aqueous solution containing 200 ppm of the ethanol was supplied at a rate of 8.8 kg/h through the exhaust pipe H arranged at the bottom of the evaporation vessel 1. The condensed ethanol which concentration reached to 94 weight % was obtained at a rate of 10 kg/h through the recovery pipe C for condensed organic compound.

EXAMPLE 18

The dehydration operation was done according to the flow sheet of FIG. 2. In this example, the method of the invention is applied to the chemical reaction system for production of an alcoholate from an alcohol and an alkali.

545 kg of an aqueous solution containing 15% of butanol and 121 kg of an aqueous solution containing 30% of sodium hydroxide was introduced into the reaction tank 11 through the starting material introducing pipe A. The reaction tank 11 was heated indirectly to a temperature of 120° C. by steam of 4 kg/cm²G supplied through the heat source supplying pipe 19, and the gaseous mixture comprising water vapor and butanol vapor flowed through the derivery pipe B. The gaseous mixture was heated to 130° C. using the heater 12, and then was supplied to the primary side of the gas separation membrane 13 under atmospheric pressure. Aromatic polyimide hollow fibers having an outer diameter of 500 μm and effective membrane area of 60 m² was employed as the gas separation membrane 13. The pressure of the secondary side of the gas separation membrane 13 was reduced to 40 mmHg. The gaseous mixture containing an increased amount of water vapor permeated into the secondary side of the gas separation membrane 13 was condensed in the condenser 16, and then transferred to the pressure reduction tank 17 to remove from the system through the exhaust pipe F.

The gaseous mixture which was not permeated through the gas separation membrane 13 was composed mainly of butanol vapor. The gaseous mixture was transferred to the condenser 14 through the delivery pipe C and condensed, and then was returned back to the reaction tank 11 through the returning pipe D of the tank 15.

After 11 hours, 484 kg of an aqueous solution containing 18% of buthylate was obtained in the reaction tank 11. The water content was 400 ppm. The gaseous mixture permeated to the gas separation membrane 13 was composed mainly of water vapor. The amount of the gaseous mixture was 182 kg, and the butanol content was approx. 2%. The whole amount of water vapor (4 kg/cm²G) supplied through the heat source supplying pipe 19 was 0.6 t.

We claim:

1. A method for dehydration and concentration of an aqueous solution containing an organic compound which is in the form of a liquid at 25° C. and has a boiling point of not higher than 200° C., comprising the steps of:

evaporating the aqueous solution to produce a gaseous mixture comprising vapor of the organic compound and vapor of water;

selectively separating the water vapor from the gaseous mixture by bringing the gaseous mixture into contact with a first side of an aromatic polyimide gas separation membrane at a temperature of 70° C. or higher to cause selective permeation of water vapor through the membrane to a second side whereby the water vapor passes selectively into the second side of the membrane, while the gaseous mixture from which water content is reduced is left on the first side where the gaseous mixture was introduced; and recovering the gaseous mixture from which water vapor content is reduced from the first side of the membrane.

2. The method as claimed in claim 1, wherein the permeation of the water vapor is performed by reducing pressure on another side of the gas separation membrane.

3. The method as claimed in claim 1, wherein the permeation of the water vapor is performed by causing a carrier gas flowing on a surface on another side of the gas separation membrane.

4. The method as claimed in claim 1, wherein the organic compound is ethanol or isopropanol.

5. The method as claimed in claim 1, wherein the aromatic polyimide comprises an aromatic tetracarboxylic acid skeleton and an aromatic diamine skeleton.

6. The method as claimed in claim 1, wherein the aromatic polyimide contains an aromatic tetracarboxylic acid skeleton derived from at least one biphenyltetracarboxlic anhydride selected from the group consisting of 3,3',4,4'-biphenyltetracarboxylic dianhydride and 2,3,3',4'-biphenyltetracarboxylic dianhydride.

7. The method as claimed in claim 1, wherein the aromatic polyimide contains an aromatic diamine skeleton derived from a diamine selected from the group consisting of 3,4'-diaminodiphenyl ether, 4,4'-diaminodiphenyl ether and diaminodiphenylmethane.

8. The method as claimed in claim 1, wherein the gas separation membrane has a thickness of from 10 μm to 200 μm.

9. The method as claimed in claim 1, wherein the gas separation membrane is an integrated membrane in the form of a hollow fiber.

10. The method as claimed in claim 1, wherein the aqueous solution contains the organic compound in an amount of not less than 50 weight %.

11. The method as claimed in claim 1, wherein the aqueous solution contains the organic compound in an amount of not less than 90 weight %.

12. The method as claimed in claim 1, wherein the organic compound is selected from the group consisting of aliphatic alcohols, alicyclic alcohols, aromatic alcohols organic carboxylic acids, esters, ketones and cyclic ethers.

13. The method as claimed in claim 1, wherein the organic compound has a boiling point of not higher than 150° C.

14. The method of claim 12, wherein the aqueous solution contains the organic compound in an amount not less than 50 weight %.

15. The method of claim 1, wherein the organic compound is methanol, ethanol, n-propanol, isopropanol, n-butanol, sec-butanol, tert-butanol, ethylene glycol, cyclohexanol, benzyl alcohol, formic acid, acetic acid, propionic acid, butyric acid, butyl acetate, ethyl acetate, acetone, methyl ethyl ketone, tetrahydrofuran, dioxane, dibutyl amine or aniline.

16. The method of claim 15, wherein the aqueous solution contains the organic compound in an amount not less than 50 weight %.

* * * * *